(12) United States Patent
Calvosa et al.

(10) Patent No.: US 10,149,704 B2
(45) Date of Patent: Dec. 11, 2018

(54) INTERVERTEBRAL DISTRACTOR

(71) Applicants: Giuseppe Calvosa, Pisa (IT); Raphael Bartalesi, Florence (IT); Miria Tenucci, Lucca (IT)

(72) Inventors: Giuseppe Calvosa, Pisa (IT); Raphael Bartalesi, Florence (IT); Miria Tenucci, Lucca (IT)

( * ) Notice: Subject to any disclaimer, the term of this patent is extended or adjusted under 35 U.S.C. 154(b) by 0 days.

(21) Appl. No.: 15/540,558

(22) PCT Filed: Dec. 2, 2015

(86) PCT No.: PCT/IB2015/059290
§ 371 (c)(1),
(2) Date: Jun. 28, 2017

(87) PCT Pub. No.: WO2016/088058
PCT Pub. Date: Jun. 9, 2016

(65) Prior Publication Data
US 2017/0348028 A1 Dec. 7, 2017

(30) Foreign Application Priority Data
Dec. 4, 2014 (IT) .............................. RM2014A0704

(51) Int. Cl.
*A61B 17/70* (2006.01)
(52) U.S. Cl.
CPC ...... *A61B 17/7065* (2013.01); *A61B 17/7067* (2013.01)
(58) Field of Classification Search
CPC ........ A61B 17/7065–17/7068; A61B 17/7067; A61F 2002/30523; A61F 2002/30525
See application file for complete search history.

(56) References Cited

U.S. PATENT DOCUMENTS 8,105,358 B2 * 1/2012 Phan ................. A61B 17/7065
606/246
8,702,757 B2 * 4/2014 Thommen .......... A61B 17/7065
606/249

(Continued)

FOREIGN PATENT DOCUMENTS

WO WO 2008044057 A1 * 4/2008 ........... A61F 2/4465
WO WO 2011141869 A1 * 11/2011 ......... A61B 17/7065

OTHER PUBLICATIONS

International Preliminary Search Report and the Written Opinion of PCT/IB2015/059290, dated Jun. 6, 2017.

(Continued)

*Primary Examiner* — Jacqueline Johanas
(74) *Attorney, Agent, or Firm* — Hershkovitz & Associates, PLLC; Abe Hershkovitz (57) ABSTRACT

An interspinous device for arthrodesis, comprising a main body of distraction, inserted between two adjacent spinous processes to provide a relative support; a first and a second pair of lateral stabilizers; support means of each of the pairs of stabilizers slidable with respect to the main body; and a threaded shaft of actuation of the lateral stabilizers, percutaneously operable to determine a rotation and a subsequent translation of the stabilizers with respect to said main body, wherein the overall arrangement is such that each stabilizer is rotatably movable relative to the main body between a first closed configuration and a second open configuration, in which the stabilizers are open wide, and between the second open configuration and a third retaining configuration, in which the open-wide stabilizers of the first pair are longitudinally juxtaposed to respective open-wide stabilizers of the second pair so as to abut a spinous process.

16 Claims, 5 Drawing Sheets

(56) References Cited

U.S. PATENT DOCUMENTS

| | | | |
|---|---|---|---|
| 8,998,955 B2* | 4/2015 | Calvosa | A61B 17/7065 |
| | | | 606/249 |
| 9,770,271 B2* | 9/2017 | Lamborne | A61B 17/7062 |
| 2008/0108990 A1 | 5/2008 | Mitchell et al. | |
| 2009/0292316 A1* | 11/2009 | Hess | A61B 17/7065 |
| | | | 606/249 |
| 2010/0152775 A1 | 6/2010 | Seifert et al. | |
| 2010/0318127 A1 | 12/2010 | Phan et al. | |
| 2011/0046674 A1* | 2/2011 | Calvosa | A61B 17/7065 |
| | | | 606/249 |
| 2011/0172710 A1* | 7/2011 | Thommen | A61B 17/7065 |
| | | | 606/249 |
| 2012/0029565 A1 | 2/2012 | Seifert et al. | |
| 2012/0150229 A1* | 6/2012 | Hess | A61B 17/7065 |
| | | | 606/249 |
| 2013/0325067 A1 | 12/2013 | Calvosa et al. | |
| 2013/0331890 A1* | 12/2013 | Calvosa | A61B 17/7065 |
| | | | 606/249 |
| 2014/0188170 A1 | 7/2014 | Zappacosta et al. | |
| 2014/0371797 A1 | 12/2014 | Seifert et al. | |
| 2015/0164656 A1 | 6/2015 | Zappacosta et al. | |
| 2016/0100865 A1* | 4/2016 | Thommen | A61B 17/7065 |
| | | | 606/249 |
| 2016/0256200 A1* | 9/2016 | Seifert | A61B 17/3468 |
| 2017/0360485 A1* | 12/2017 | Lamborne | A61B 17/7062 |

OTHER PUBLICATIONS

International Search Report and the Written Opinion of PCT/IB2015/059290, dated Sep. 6, 2016

* cited by examiner

INTERVERTEBRAL DISTRACTOR

TECHNICAL FIELD OF THE INVENTION

The present invention relates to a distractor device for arthrodesis, interspinous, suitable for a percutaneous insertion.

The device of the invention is of the type comprising a double pair of lateral stabilizers, selectively movable between a closed compact configuration and a wide-open configuration suitable to stabilize the device between two adjacent spinous processes, blocking the relative movement thereof.

BACKGROUND

The interspinous intervertebral distractors are devices apt to space two adjacent vertebrae, and may be designed for permanent implantation in the space between the spinous processes of said vertebrae.

Typically, the interspinous devices have the purpose of keeping an intervertebral distraction so as to limit the loads transmitted between the vertebrae due to, for example, degenerative diseases of the intervertebral disk, and to contain the associated painful manifestations.

In addition, the interspinous distractors may be used for spinal arthrodesis (fusion), i.e., to inhibit relative movements between adjacent vertebrae, making the articulation static (i.e. fixed) instead of mobile.

Compared to other spinal implants, the interspinous distractors can be easily inserted in situ, thanks to the relative ease with which the spinous processes of two adjacent vertebrae allow little divarications.

To ensure a stable position between the vertebrae, the distractor is typically equipped with side flaps suitable to abut on the spinous processes.

US 2008/0108990 A1 describes an interspinous implant which comprises two side stops, each defined by four segments pivotally connected at respective ends. The implant also comprises a central spacer disposed between stops and an auction rod which passes through the spacer.

US 2010/0318127 A1 describes an interspinous implant comprising a central body, two lateral wings rotatable on a longitudinal axis of the central body and a rod connected to the wings by means of a threaded connection.

US 2014/0188170 A1 describes a system of fixing of a spinous process based on an expandable central body.

US 2013/0325067 A1 describes an interspinous device equipped with a central body and rotatable lateral distractors.

However, the known distractors have some drawbacks still unsolved.

In particular, the need to spread apart in situ the above-mentioned stabilizing flaps has so far resulted in mechanically complex systems and/or devices that are not very structurally resistant, making some distractors globally unreliable.

The complexity of systems so far proposed constitutes a significant restriction even for the purpose of miniaturization of the distractor, for example, for individuals of small stature or infant age.

A further problem is then represented by the tools necessary to perform the above mentioned spreading apart, often too complex and rather complicated to operate percutaneously, at the expense of the speed of the intervention.

SUMMARY OF THE INVENTION

The technical problem posed and solved by the present invention is to provide an interspinous device which obviates the drawbacks mentioned above with reference to prior art.

This problem is solved by an interspinous distractor device for fusion in arthrodesis, comprising a main distractor body configured to be inserted between two adjacent spinous processes to provide a support therebetween; a first pair of lateral stabilizers and a second pair of lateral stabilizers, which first pair and second pair are arranged spaced apart along a longitudinal direction of the main distractor body; support elements of each of the first pair and second pair of lateral stabilizers, which support elements are slidable with respect to the main distractor body along the longitudinal direction. The lateral stabilizers of each of the first pair and second pair are rotatably connected to a respective support element of the support elements according to respective axes perpendicular to the longitudinal direction. The lateral stabilizers of each of the first pair and second pair are slidable integrally to the respective support elements. An actuation system for actuating the lateral stabilizers of the first pair and second pair is percutaneously operable to determine a rotation and a subsequent translation of the lateral stabilizers with respect to the main distractor body. The actuation system comprises a threaded shaft rotatable about an axis extending along the longitudinal direction, which threaded shaft has a first thread and a second thread. The first thread and second thread are longitudinally spaced apart from one another and longitudinally opposed to one another, each thread of the first thread and second thread are configured for mating with a respective first pair or second pair of lateral stabilizers, each of the lateral stabilizers having engagement elements for mating with a respective thread of the first thread and second thread. The interspinous distractor device is configured such that each lateral stabilizer of the first pair and second pair is rotatably movable with respect to the main distractor body between a first closed configuration, wherein the lateral stabilizers realize a compact configuration which facilitates the percutaneous insertion of the interspinous distractor device, and a second open configuration, wherein the lateral stabilizers are divaricated. The interspinous distractor device is also configured such that each lateral stabilizer is slidably movable along the longitudinal direction between the second open configuration and a third retaining configuration wherein divaricated lateral stabilizers of the first pair are longitudinally juxtaposed to respective divaricated lateral stabilizers of the second pair so as to abut a spinous process. Wherein in the third retaining configuration, the lateral stabilizers of the first pair are longitudinally approached to the lateral stabilizers of the second pair with respect to the second open configuration. Control components suitable to determine a passage from the second open configuration to the third retaining configuration, which control components comprise elements configured to provide an end-of-stroke for a movement of divarication of said lateral stabilizers, which elements are configured to provide an end-of-stroke are arranged at the support elements.

Preferred features of the present invention are further embodied in the claims.

The invention provides an interspinous distractor device, particularly suitable for arthrodesis, which is minimally invasive and of simple and reliable mechanically actuation. In particular, the device of the invention provides two pairs of stabilizers, each preferably in the form of a fin, and corresponding actuation means of the stabilizers according to movements of rotation and translation. Such means is suitable to determine a movement of the stabilizers from a closed configuration of minimum encumbrance to an open-wide operative configuration and from the latter to a configuration of retention in which the open-wide stabilizers are pushed together and grip the spinous processes.

In a preferred embodiment, the actuation means has a particularly simple and at the same time robust construction, on the basis of a single oblong element that allows the simultaneous divergence of stabilizers and their subsequent translation. This element is percutaneously maneuverable from the outside in a simple and effective way.

In an even more preferred embodiment, said oblong element consists of a screw nut shaft having two opposite threads and movable in rotation and translation within a main body of the distractor device. The threads engage respective gear teeth of the stabilizers. In addition, the stabilizers can be brought on respective supports of translation.

The above mentioned three main configurations of the device are defined by the position of the stabilizers and the relative supports of translation. In particular:

in the first closed configuration, or of minimum overall dimensions, the transverse encumbrance of the device is such as to allow the insertion in a cannulated positioning instrumentation; preferably, in this configuration, the outer diameter of the device, and in general its transverse section, is almost constant along a main longitudinal axis of said device;

in the second open or open-wide configuration, the stabilizers have been rotated towards the outside of the main body by actuating the screw nut shaft which engages teeth of each stabilizer; and in the third configuration of positioning, for osteosynthesis and retention, the rotation of the screw nut shaft has produced a translation in a direction of mutual approach of the stabilizers with the supports integral to them, until dedicated tips of the stabilizers stick in the cortical bone of the spinous processes.

Preferably, the position of maximum opening of the second configuration is defined by an end-of-stroke element, preferably an abutment element, of each stabilizer on the respective support of translation.

Furthermore, the device can be locked in the third configuration of retention on the bone by dedicated means.

The device of the invention allows:

an insertion between the spinous processes of a pair of lumbar vertebrae in a minimally invasive way, preferably with a lateral-sideward surgical approach;

a fixed and constant distraction of the spinous processes for a specific length of time, necessary to ensure the arthrodesis process, i.e., melting in congruous position; and in a preferred embodiment, a facilitation of the arthrodesis process by the application of material favoring bone growth (bone of chemical synthesis) between the spinous processes.

Other advantages, features and the modes of employ of the present invention will be evident from the following detailed description of some embodiments, shown by way of example and not for limitative purposes.

BRIEF DESCRIPTION OF FIGURES

Reference will be made to the figures of the enclosed drawings, wherein.

The dimensions and the curvatures shown in the figures introduced above are to be understood as purely exemplary, and are generally magnified and not necessarily shown in proportion.

DETAILED DESCRIPTION OF PREFERRED EMBODIMENTS

With reference to FIGS. 1 to 4B, an interspinous distractor device according to a preferred embodiment of the invention is designated as a whole with 1.

The device 1 is adapted to percutaneous insertion and, in the present example, it is specifically suitable for interventions of arthrodesis (bone fusion).

The device 1 firstly comprises a main body 2, extending in a longitudinal direction L. Such direction L also identifies, in the figures, a main axis of the device 1. In the present embodiment, the main body 2 has a central part 201 adapted to be placed between two adjacent spinous processes to provide a relative support. From the central part 201, two lateral oblong walls 202 and 203, respectively distal and proximal, branch off from longitudinally opposite parts.

Figure 3:
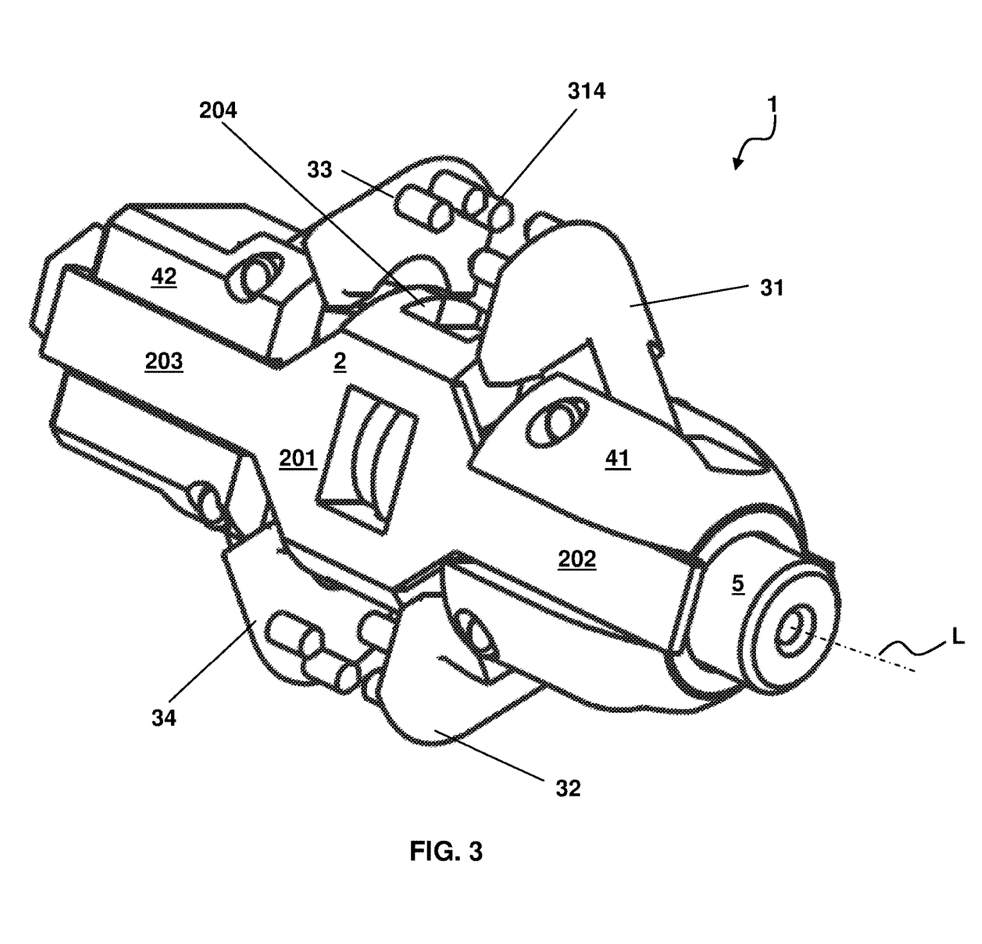
FIG. 3 shows a perspective view of the device of FIG. 1, in a different operative configuration, wherein the lateral stabilizers are open-wide and longitudinally approached.

The main body 2, particularly in its central part 201, includes a plurality of openings or windows 204 to permit affixing of material for bone regrowth, in particular autologous/heterologous bone. With reference for example to FIG. 3, the windows 204 are represented as superior. The other windows shown as "lateral" may be used for the attachment of maneuvering instrumentation.

The device 1 also comprises a first pair—defined as distal—of stabilizers, denoted by 31 and 32, and a second pair—proximal—of stabilizers, denoted by 33 and 34. The two pairs of stabilizers are arranged longitudinally spaced along the direction L, on opposite sides of the central part 201 of the main body 2, and each at a respective side part 202, 203 of the main body 2. In addition, the stabilizers 31, 32 and 33, 34 of each pair are positioned on opposite sides with respect to the axis L.

In the present example, each stabilizer 31-34 presents in substantially the form of a fin or a paddle. Since the four stabilizers can be the same, in the following, for brevity, only the stabilizer denoted by 31 will be described, its description being valid also for the other three stabilizers 32, 33 and 34. The fins/paddles may present different arrangement and shape of teeth to avoid that, during the closing of the device which will be discussed shortly, facing teeth can come into contact with and overwhelm the fragility of the spinous process.

Figure 1:
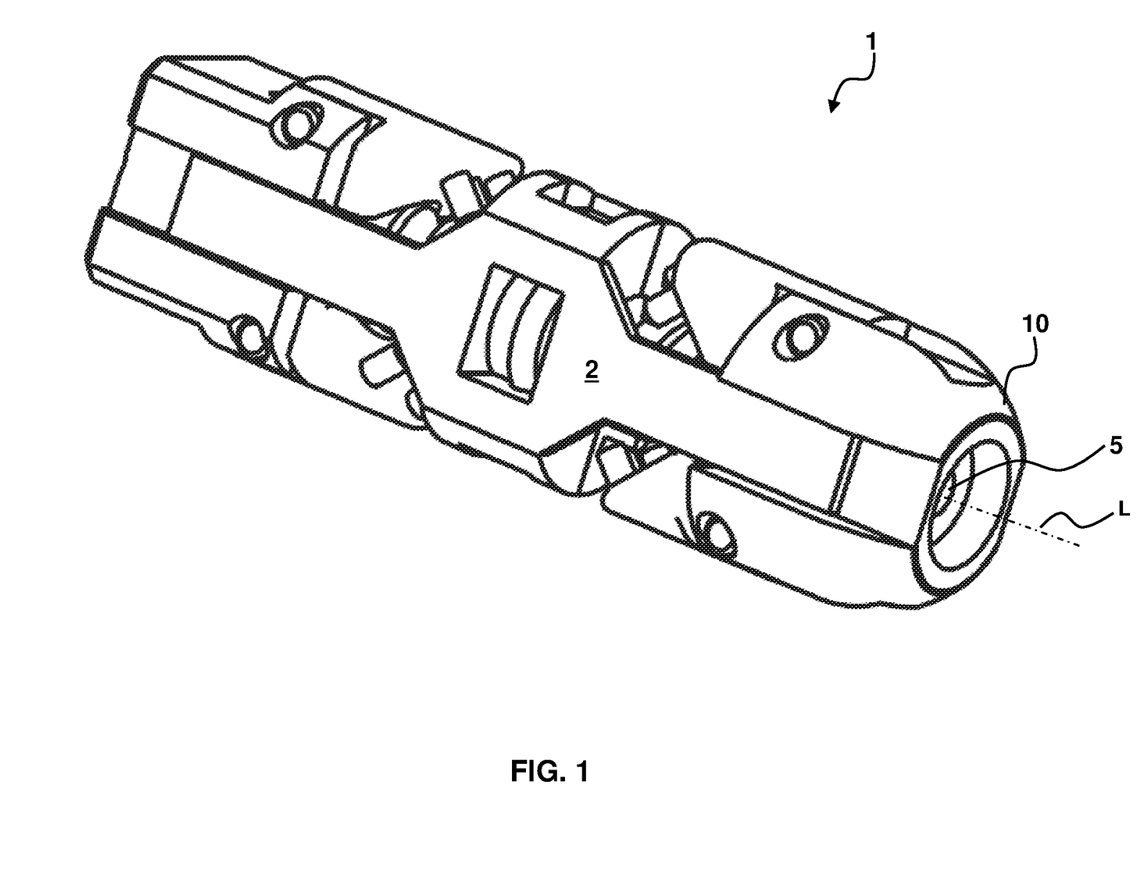
FIG. 1 shows a perspective view of a preferred embodiment of the interspinous distractor device of the invention, in a first configuration of minimum encumbrance designed for insertion into the patient's body, wherein the lateral stabilizers are closed.
Figure 2A:
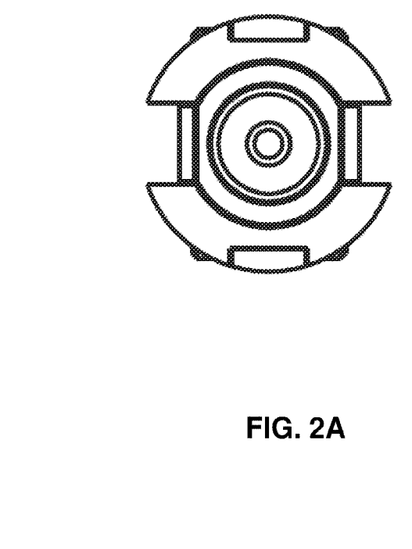
FIGS. 2A and 2B show the device of FIG. 1, respectively a front (distal) view and a longitudinal section thereof.
Figure 2B:
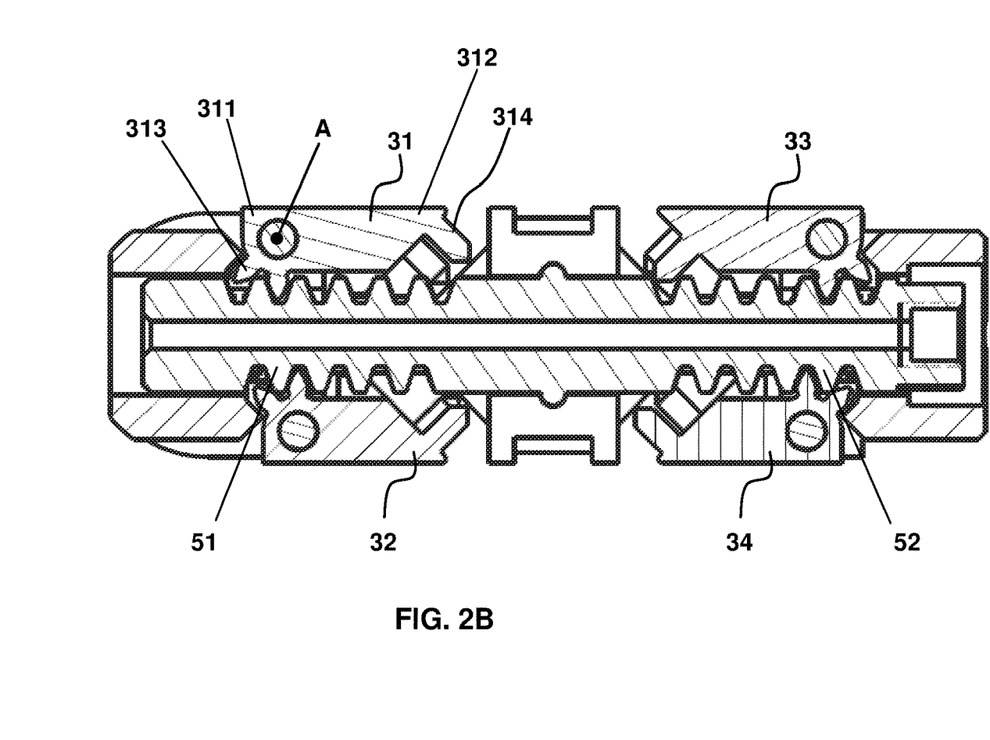

As best seen for example in FIG. 2B, with respect to the longitudinal axis L of the device, the stabilizer 31 bears a first end portion 311 rotatably connected, and in particular hinged, to the remaining part of the device 1, so as to be rotatable about a transverse axis A orthogonal to the longitudinal direction L. The axes of rotation of the four stabilizers 31-34 are parallel to each other.

During operation of the device 1, the first portion 311 remains in a substantially proximal position with respect to the longitudinal axis L.

In correspondence to the first portion 311, the stabilizer 31 is provided with a part shaped as a toothed wheel sector and bearing gear teeth 313, whose function will be shortly explained.

The stabilizer 31 also comprises a second end portion 312, which, during operation of the device 1 as will be described later, is adapted to assume a distal position with respect to the longitudinal axis L. The end portion 313 bears engagement means of a spinous process. In the present example, such means are in the form of one or more teeth or pins 314, and in general of elements bearing a pointed end. In the embodiment shown, three elements are provided.

The device 1 further comprises support means of the pairs of stabilizers, which support means is configured to slide in a direction L with respect to the main body 2.

In the present example, these support means comprise a first support body 41 and a second support body 42, arranged longitudinally spaced along the axis L and each connected to the stabilizers of a respective pair 31, 32 or 33, 34. In particular, the stabilizers of each pair 31, 32 or 33, 34 are rotatably connected to a respective support body 41 or 42.

The sliding of the stabilizers 31-34 determines an integral sliding of the support means 41, 42.

The components of the device 1, and in particular the main body 2 and the distal support body 41, define a distal part of the same device bearing a tapered penetration profile 10, in particular a rounded profile.

The device 1 also comprises actuation means of the stabilizers, operable by an operator to determine a rotation of the stabilizers 31-34 and a subsequent translation of the stabilizers and the support bodies 41 and 42 associated therewith with respect to the main body 2.

Figure 4A:
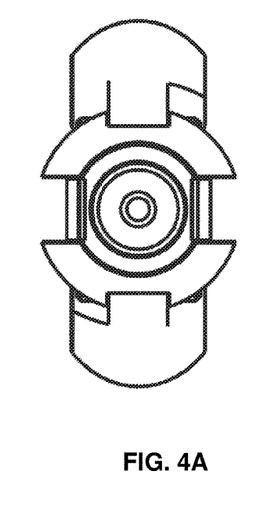
FIGS. 4A and 4B show the device of FIG. 3, respectively a front (distal) view and a longitudinal section thereof.
Figure 4B:
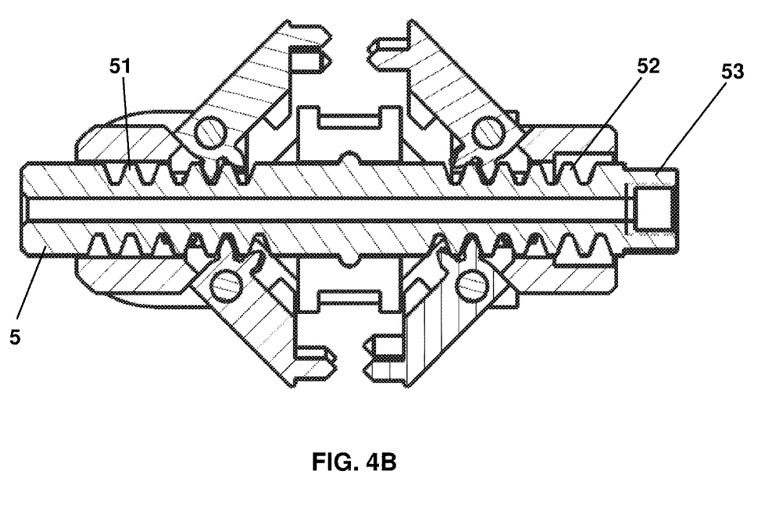

With particular reference to FIG. 4B, in the present embodiment, the actuation means comprises a threaded shaft, or a screw nut shaft, 5 rotatable and translatable around/along the longitudinal axis L with respect to the main body 2 and the support bodies 41 and 42. In particular, the threaded shaft 5 is received and movable within such main body 2 and support bodies 41 and 42.

The threaded shaft 5 has a first and a second thread, respectively 51 and 52, longitudinally spaced and mutually opposite. Each thread 51, 52 is configured for coupling with the gear portion 311 of stabilizers of a respective pair 31, 32 or 33, 34. In particular, in the present example, each stabilizer forms with the respective thread of the screw nut shaft a worm screw system—ring gear, preferably of helical profile. The opposed thread of screw nut shaft 5 allows the opening of both pairs of stabilizers with only one direction of rotation of the shaft.

The threaded shaft 5 has a proximal portion 53 apt to be coupled with a manipulation tool operable percutaneously.

Figure 4C:
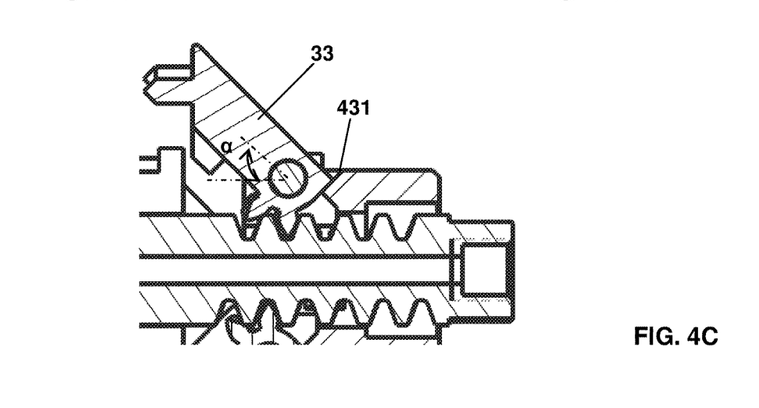
FIG. 4C shows an enlarged detail of the view of FIG. 4B.

As better visible even in the detail of FIG. 4C, at each support body 41, 42, for each stabilizer of the respective pair, is provided an abutment profile, denoted by 431 for the first support body 41 in the interaction with the stabilizer 33. This profile determines a limit switch in a movement of rotation towards the outside—that is to say away from the longitudinal axis L—of the stabilizer with respect to the respective support body and the main body 2.

The overall arrangement of parts of the device 1 as described so far is such that the same device is suitable to assume three distinct principal configurations, as shown below.

A first configuration of minimum encumbrance, or closed, is shown in FIGS. 1, 2A, 2B and 5A. In this first configuration, the stabilizers are rotated toward the main body 2 so as to be substantially lying along the direction L. In particular, the arrangement is such that the free ends of the first stabilizers 31, 33 of the two pairs and the free ends of the second stabilizers 32, 34 of the two pairs are positioned facing and adjacent to the central part 201 of the main body 2. Thus, the pivotal connections of the stabilizers to the supporting bodies are arranged outwardly with respect to the central part 201 of the main body 2. In this configuration, the screw nut shaft 5 is maximally set back in the proximal direction. More specifically, the shaft 5 is rotated in such a way that the supports 41 and 42 are moved away from the central body 201 and the fins 31-34 are closed and arranged substantially lying along the direction L.

Figure 5A:
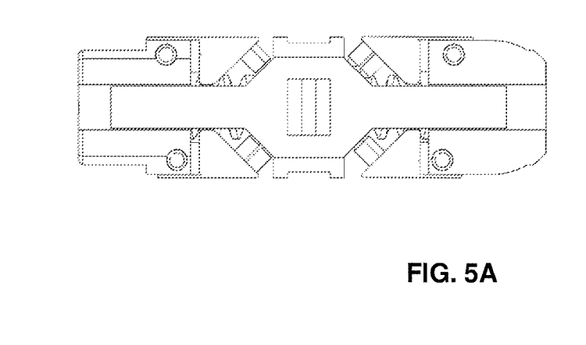
FIGS. 5A, 5B and 5C show a schematic representation of the device of FIG. 1, respectively a first configuration of minimum encumbrance, a second open-wide configuration and the configuration of the longitudinally-approached stabilizers, the latter for retention on inserting over spinous processes.

In the closed configuration here considered, the distal rounded profile 10 and the lying arrangement of the stabilizers favor the percutaneous insertion of the device into the patient's body. Such insertion can occur by cannula and/or guide wires in accordance with procedures already known. Once the true insertion step is completed, the main body 2 is housed between two adjacent spinous processes, as shown in FIG. 5A.

Figure 5B:
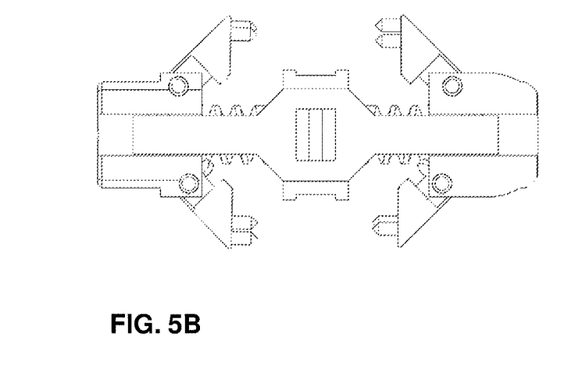
Figure 5C:
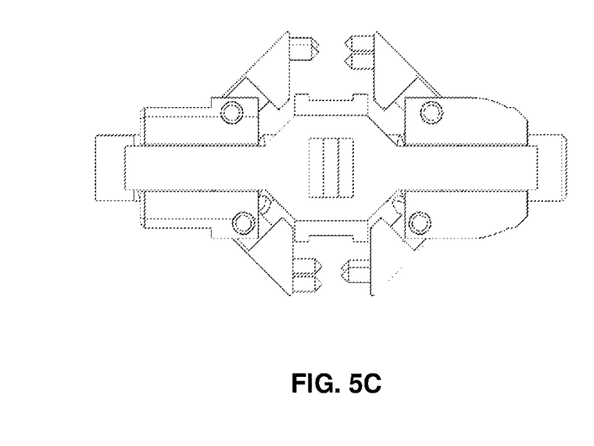

A second opening or open-wide configuration is shown in FIG. 5B (but appreciable also in FIGS. 3, 4A, 4B, 4C and 5C, which represent a third configuration of evolution of the second configuration considered here). In this second configuration, the stabilizers are precisely open wide, that is, rotated towards the outside of the main body 2, so that their free ends move away from the main body 2 and the longitudinal axis L.

The transition from the first configuration to the second configuration, that is, the rotation of the stabilizers toward the outside of the main body 2, is obtained by percutaneously actuating the screw nut shaft 5 by means of an external tool, for example a screwdriver. In particular, by rotating shaft 5, it moves toward the distal end within the main body 2 and the support bodies 41 and 42. The engagement of the threads 51 and 52 with the respective gear teeth 313 of the four stabilizers precisely determines a rotation of the stabilizers, in opposite directions for the two pairs of stabilizers. This second configuration is obtainable, as well as with a screwdriver, with a special instrumentation which prevents the translation of the bodies 41 and 42 during actuation of the nut screw 5.

The abutment end-of-stroke elements 431 determine the position of maximum opening of the stabilizers. In the present example, in this configuration of maximum opening, each stabilizer encloses an angle $\alpha$ of about 45 degrees with respect to the direction L.

A third configuration of retention is shown in FIGS. 3, 4A, 4B, 4C and 5C. In this third configuration, the open-wide stabilizers of the first pair 31, 32 are longitudinally juxtaposed to respective open-wide stabilizers 33, 34 of the second pair so as to fit on a spinous process. The transition from the second to the third configuration is obtained by continuing to rotate the screw nut shaft 5 and keeping it stationary with respect to translations. In this way, the rotation of the shaft 5 determines, by virtue of the limit switch of rotation defined by profiles 431, the movement of the stabilizers and the support bodies 41 and 42 attached to them, along the shaft 5 in the direction L. The direction of this motion is opposite for the two pairs of stabilizers, resulting in a mutual approach of them. This translation is stopped when the engagement elements 314 penetrate the cortical bone of the spinous processes between which is arranged the central part 201 of the main body 2. The transition to the third configuration is obtained, disconnecting the device from the instrument that blocks the translation.

It will be appreciated that a single instrument. percutaneously operated, is sufficient to run the divergence of both pairs of stabilizers and for their subsequent translation.

Other embodiments may provide means of engagement between stabilizers and shaft, or actuating means, different from those described above.

Furthermore, the device of the invention can comprise control means suitable to determine a transition from said second configuration to said third configuration different from the end-of-stroke elements mentioned above.

Still further, a locking system of the supports of translation of the device, or stabilizers, can be provided in the third configuration to prevent the possible distancing of the respective pairs.

The present invention has hereto been described with reference to preferred embodiments. It is to be understood that there may be other embodiments afferent to the same inventive core, as defined by the scope of protection of the claims set out below.

The invention claimed is:

1. An interspinous distractor device for arthrodesis, comprising:
  a main distractor body, configured to be inserted between two adjacent spinous processes to provide a support therebetween;
  a first pair of lateral stabilizers and a second pair of lateral stabilizers, which first pair and second pair are arranged spaced apart along a longitudinal direction of said main distractor body;
  support elements of each of said first pair and second pair of lateral stabilizers, which support elements are slidable with respect to said main distractor body along said longitudinal direction,
  wherein the lateral stabilizers of each of said first pair and second pair are rotatably connected to a respective support element of said support elements according to respective axes perpendicular to said longitudinal direction and wherein said lateral stabilizers of each of said first pair and second pair are slidable integrally to said respective support elements;
  an actuation system for actuating said lateral stabilizers of said first pair and second pair, which actuation system is percutaneously operable to determine a rotation and a subsequent translation of said lateral stabilizers with respect to said main distractor body, which actuation system comprises a threaded shaft rotatable about an axis extending along said longitudinal direction, which threaded shaft has a first thread and a second thread, said first thread and second thread being longitudinally spaced apart from one another and longitudinally opposed to one another, each thread of said first thread and second thread being configured for mating with a respective first pair or second pair of lateral stabilizers, each of said lateral stabilizers having engagement elements for mating with a respective thread of said first thread and second thread,
  wherein the interspinous distractor device is configured such that each lateral stabilizer of said first pair and second pair is rotatably movable with respect to said main distractor body between a first closed configuration, wherein the lateral stabilizers realize a compact configuration which facilitates the percutaneous insertion of the interspinous distractor device, and a second open configuration, wherein the lateral stabilizers are divaricated,
  and wherein the interspinous distractor device is also configured such that each lateral stabilizer is slidably movable along said longitudinal direction between said second open configuration and a third retaining configuration wherein divaricated lateral stabilizers of the first pair are longitudinally juxtaposed to respective divaricated lateral stabilizers of the second pair so as to abut a spinous process, wherein in said third retaining configuration, the lateral stabilizers of said first pair are longitudinally approached to the lateral stabilizers of the second pair with respect to said second open configuration; and
  control components suitable to determine a passage from said second open configuration to said third retaining configuration, which control components comprise elements configured to provide an end-of-stroke for a movement of divarication of said lateral stabilizers, which elements configured to provide an end-of-stroke are arranged at said support elements.

2. The device according to claim 1, wherein each of said lateral stabilizers is substantially in the form of a fin.

3. The device according to claim 2, wherein said threaded shaft is a nut screw shaft.

4. The device according to claim 3, wherein said threaded shaft is slidable within said main distractor body.

5. The device according to claim 1, wherein said threaded shaft is a nut screw shaft.

6. The device according to claim 5, wherein said threaded shaft is slidable within said main distractor body.

7. The device according to claim 1, wherein each of said engagement elements is in the form of gear teeth suitable for mating with the respective thread of said first and second thread of said actuation system.

8. The device according to claim 7, wherein each of said lateral stabilizers has an end portion shaped as a toothed wheel sector.

9. The device according to claim 1, wherein said actuation system has a proximal end portion configured to be coupled with a manipulation tool operable percutaneously.

10. The device according to claim 1, wherein each of said lateral stabilizers has an end portion provided with an element for engaging a spinous process, which end portion is arranged distally with respect to said main distractor body in said second open configuration and said third retaining configuration.

11. An interspinous distractor device for arthrodesis, comprising:
  a main distractor body adapted to be inserted between two adjacent spinous processes to provide a support therebetween;

a first pair of lateral stabilizers and a second pair of lateral stabilizers, which first pair and second pair are arranged spaced apart along a longitudinal direction of said main distractor body;

support elements of each of said first pair and second pair of lateral stabilizers, which support elements are slidable with respect to said main distractor body along said longitudinal direction, wherein the lateral stabilizers of each of said first pair and second pair are rotatably connected to a respective support element of said support elements according to respective axes perpendicular to said longitudinal direction and wherein said lateral stabilizers of each of said first pair and second pair are slidable integrally to said respective support elements;

an actuation system for actuating said lateral stabilizers of said first pair and second pair, which actuation system is percutaneously operable to determine a rotation and a subsequent translation of said lateral stabilizers with respect to said main distractor body, which actuation system comprises a threaded shaft rotatable about an axis extending along said longitudinal direction, which threaded shaft has a first thread and a second thread, said first thread and second thread being longitudinally spaced apart from one another and longitudinally opposed to one another, each thread of said first thread and second thread being configured for mating with a respective one of, first pair or second pair of lateral stabilizers, each of said lateral stabilizers having engagement elements capable of mating with a respective thread of said first thread and second thread, wherein the interspinous distractor device is configured such that each lateral stabilizer of said first pair and second pair is rotatably movable with respect to said main distractor body between a first closed configuration, wherein the lateral stabilizers realize a compact configuration which facilitates the percutaneous insertion of the interspinous distractor device, and a second open configuration, wherein the lateral stabilizers are divaricated, and wherein the interspinous distractor device is also configured such that each lateral stabilizer is slidably movable along said longitudinal direction between said second open configuration and a third retaining configuration wherein divaricated lateral stabilizers of the first pair are longitudinally juxtaposed to respective divaricated lateral stabilizers of the second pair so as to abut a spinous process, wherein in said third retaining configuration, the lateral stabilizers of said first pair are longitudinally approached to the lateral stabilizers of the second pair with respect to said second open configuration; and control components suitable to determine a passage from said second open configuration to said third retaining configuration, which control components comprise elements configured to provide an end-of-stroke for a movement of divarication of said lateral stabilizers, which elements configured to provide an end-of-stroke are arranged at said support elements, wherein each of said engagement elements is in the form of gear teeth suitable for mating with the respective thread of said first thread and second thread of said actuation system.

12. The device according to claim 11, wherein each of said lateral stabilizers has an end portion shaped as a toothed wheel sector.

13. The device according to claim 11, wherein said actuation system has a proximal end portion configured to be coupled with a manipulation tool operable percutaneously.

14. The device according to claim 11, wherein each of said lateral stabilizers has an end portion provided with an element for engaging a spinous process, which end portion is arranged distally with respect to said main distractor body in said second open configuration and said third retaining configuration.

15. The device according to claim 11, wherein said threaded shaft is a nut screw shaft.

16. The device according to claim 11, wherein said threaded shaft is slidable within said main distractor body.

\* \* \* \* \*